United States Patent
Truncale et al.

(10) Patent No.: US 7,488,348 B2
(45) Date of Patent: Feb. 10, 2009

(54) CARTILAGE ALLOGRAFT PLUG

(75) Inventors: Katherine G. Truncale, Hillsborough, NJ (US); Moon Hae Sunwoo, Old Tappan, NJ (US); Arthur A. Gertzman, Stony Point, NY (US); William W. Tomford, Belmont, MA (US); Judith I. Yannariello-Brown, Somerset, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 86 days.

(21) Appl. No.: 11/151,270

(22) Filed: Jun. 14, 2005

(65) Prior Publication Data

US 2005/0251268 A1    Nov. 10, 2005

Related U.S. Application Data

(63) Continuation-in-part of application No. 10/438,883, filed on May 16, 2003.

(51) Int. Cl.
  *A61F 2/28* (2006.01)
(52) U.S. Cl. .................................. 623/23.63
(58) Field of Classification Search ............. 623/11.11, 623/16.11, 17.11, 17.16, 23.56, 23.57, 23.58, 623/23.59, 23.6, 23.61, 23.62, 23.63, 14.12, 623/20.14
  See application file for complete search history.

(56) References Cited

U.S. PATENT DOCUMENTS

| | | | |
|---|---|---|---|
| 3,400,199 A | 9/1968 | Balassa | |
| 4,172,128 A | 10/1979 | Thiele et al. | |
| 4,501,269 A | 2/1985 | Bagby | |
| 4,627,853 A | 12/1986 | Campbell et al. | |
| 4,642,120 A | 2/1987 | Nevo et al. | |
| 4,656,137 A | 4/1987 | Balassa | |
| 4,681,763 A | 7/1987 | Nathanson et al. | |
| 4,757,017 A | 7/1988 | Cheung | |
| 4,776,173 A | 10/1988 | Kamarei et al. | |
| 4,776,853 A | 10/1988 | Klement et al. | |

(Continued)

FOREIGN PATENT DOCUMENTS

EP    0522569 A1    1/1993

(Continued)

OTHER PUBLICATIONS

Translation of WO 99/21497A1.*

(Continued)

*Primary Examiner*—Anu Ramana
(74) *Attorney, Agent, or Firm*—Greenberg Traurig, LLP

(57) ABSTRACT

The invention is directed toward a cartilage repair assembly comprising a cylindrically shaped allograft structure of subchondral bone with an integral overlying smaller diameter cartilage cap which is treated to remove cellular debris and proteoglycans. The shaped structure is dimensioned to fit in a drilled bore in a cartilage defect area so that the subchondral bone of the structure engages the side wall of the bone portion of the drilled bore in an interference fit while the cartilage cap is spaced from cartilage portion of the side wall of the drilled bore forming a gap in which a milled cartilage and biocompatible carrier mixture is placed allowing cell transfer throughout the defect area. A method for inserting the shaped allograft structure into a cartilage defect area is also disclosed.

26 Claims, 2 Drawing Sheets

U.S. PATENT DOCUMENTS

| | | | |
|---|---|---|---|
| 4,801,299 A | 1/1989 | Brendel et al. |
| 4,902,508 A | 2/1990 | Badylak et al. |
| 4,932,973 A | 6/1990 | Gendler |
| 4,950,296 A | 8/1990 | McIntyre |
| 5,041,138 A | 8/1991 | Vacanti et al. |
| 5,053,049 A | 10/1991 | Campbell |
| 5,067,964 A | 11/1991 | Richmond et al. |
| 5,073,373 A | 12/1991 | O'Leary et al. |
| 5,152,791 A | 10/1992 | Hakamatsuka et al. |
| 5,195,892 A | 3/1993 | Gersberg |
| 5,206,023 A | 4/1993 | Hunziker |
| 5,236,456 A | 8/1993 | O'Leary et al. |
| 5,256,140 A | 10/1993 | Fallick |
| 5,270,300 A | 12/1993 | Hunziker |
| 5,275,826 A | 1/1994 | Badylak et al. |
| 5,290,558 A | 3/1994 | O'Leary et al. |
| 5,306,311 A | 4/1994 | Stone et al. |
| 5,314,476 A | 5/1994 | Prewett et al. |
| 5,326,357 A | 7/1994 | Kandel |
| 5,336,616 A | 8/1994 | Livesey et al. |
| 5,354,557 A | 10/1994 | Oppermann et al. |
| 5,356,629 A | 10/1994 | Sander et al. |
| 5,368,858 A | 11/1994 | Hunziker |
| 5,496,722 A | 3/1996 | Goodwin et al. |
| 5,507,813 A | 4/1996 | Dowd et al. |
| 5,516,532 A | 5/1996 | Atala et al. |
| 5,624,463 A | 4/1997 | Stone et al. |
| 5,632,745 A | 5/1997 | Schwartz |
| 5,695,998 A | 12/1997 | Badylak et al. |
| 5,700,774 A | 12/1997 | Hattersley et al. |
| 5,707,962 A | 1/1998 | Chen et al. |
| 5,723,331 A | 3/1998 | Tubo et al. |
| 5,736,372 A | 4/1998 | Vacanti et al. |
| 5,749,874 A | 5/1998 | Schwartz |
| 5,759,190 A | 6/1998 | Vibe-Hansen et al. |
| 5,769,899 A | 6/1998 | Schwartz et al. |
| 5,770,417 A | 6/1998 | Vacanti et al. |
| 5,782,835 A * | 7/1998 | Hart et al. .................. 606/79 |
| 5,782,915 A | 7/1998 | Stone |
| 5,786,217 A | 7/1998 | Tubo et al. |
| 5,800,537 A | 9/1998 | Bell |
| 5,814,084 A | 9/1998 | Grivas et al. |
| 5,846,931 A | 12/1998 | Hattersley et al. |
| 5,853,746 A | 12/1998 | Hunziker |
| 5,855,620 A | 1/1999 | Bishopric et al. |
| 5,863,296 A | 1/1999 | Orton |
| 5,866,415 A | 2/1999 | Villeneuve |
| 5,893,888 A | 4/1999 | Bell |
| 5,899,936 A | 5/1999 | Goldstein |
| 5,904,716 A | 5/1999 | Gendler |
| 5,906,827 A | 5/1999 | Khouri et al. |
| 5,910,315 A | 6/1999 | Stevenson et al. |
| 5,916,265 A | 6/1999 | Hu |
| 5,964,805 A | 10/1999 | Stone |
| 5,972,368 A | 10/1999 | McKay |
| 5,989,269 A | 11/1999 | Vibe-Hansen et al. |
| 6,013,853 A | 1/2000 | Athanasiou et al. |
| 6,027,743 A | 2/2000 | Khouri et al. |
| 6,030,635 A | 2/2000 | Gertzman et al. |
| 6,039,762 A | 3/2000 | McKay |
| 6,090,998 A | 7/2000 | Grooms et al. |
| 6,096,081 A | 8/2000 | Grivas et al. |
| 6,096,347 A | 8/2000 | Geddes et al. |
| 6,110,209 A | 8/2000 | Stone |
| 6,110,482 A | 8/2000 | Khouri et al. |
| 6,143,293 A | 11/2000 | Weiss et al. |
| 6,183,737 B1 | 2/2001 | Zaleske et al. |
| 6,197,586 B1 | 3/2001 | Bhatnagar et al. |
| 6,235,316 B1 | 5/2001 | Adkisson |
| 6,251,143 B1 | 6/2001 | Schwartz et al. |
| 6,258,778 B1 | 7/2001 | Rodgers et al. |
| 6,294,187 B1 | 9/2001 | Boyce et al. |
| 6,319,712 B1 | 11/2001 | Meenen et al. |
| 6,352,558 B1 | 3/2002 | Spector |
| 6,376,244 B1 | 4/2002 | Atala |
| 6,379,367 B1 | 4/2002 | Vibe-Hansen et al. |
| 6,379,385 B1 | 4/2002 | Kalas et al. |
| 6,383,221 B1 | 5/2002 | Scarborough et al. |
| 6,398,811 B1 | 6/2002 | McKay |
| 6,437,018 B1 | 8/2002 | Gertzman et al. |
| 6,440,141 B1 | 8/2002 | Philippon |
| 6,468,314 B2 | 10/2002 | Schwartz |
| 6,488,033 B1 | 12/2002 | Cerundolo |
| 6,489,165 B2 | 12/2002 | Bhatnagar |
| 6,511,958 B1 | 1/2003 | Atkinson et al. |
| 6,514,514 B1 | 2/2003 | Atkinson et al. |
| 6,520,964 B2 | 2/2003 | Tallarida et al. |
| 6,530,956 B1 | 3/2003 | Mansmann |
| 6,569,172 B2 | 5/2003 | Asculai et al. |
| 6,576,015 B2 | 6/2003 | Geistlich et al. |
| 6,582,960 B1 | 6/2003 | Martin et al. |
| 6,592,599 B2 | 7/2003 | Vibe-Hansen et al. |
| 6,599,300 B2 | 7/2003 | Vibe-Hansen et al. |
| 6,599,301 B2 | 7/2003 | Vibe-Hansen et al. |
| 6,623,963 B1 | 9/2003 | Muller et al. |
| 6,652,593 B2 | 11/2003 | Boyer, II et al. |
| 6,652,872 B2 | 11/2003 | Nevo et al. |
| 6,662,805 B2 | 12/2003 | Frondoza et al. |
| 6,689,747 B2 | 2/2004 | Filvaroff et al. |
| 6,727,224 B1 | 4/2004 | Zhang et al. |
| 6,730,314 B2 | 5/2004 | Jeschke et al. |
| 6,734,018 B2 | 5/2004 | Wolfinbarger, Jr. et al. |
| 6,752,834 B2 | 6/2004 | Geistlich et al. |
| 6,761,739 B2 | 7/2004 | Shepard |
| 6,761,887 B1 | 7/2004 | Kavalkovich et al. |
| 6,767,369 B2 * | 7/2004 | Boyer et al. .............. 623/23.63 |
| 6,815,416 B2 | 11/2004 | Carney et al. |
| 6,838,440 B2 | 1/2005 | Stiles |
| 6,841,150 B2 | 1/2005 | Halvorsen et al. |
| 6,852,125 B2 | 2/2005 | Simon et al. |
| 6,852,331 B2 | 2/2005 | Lai et al. |
| 6,858,042 B2 | 2/2005 | Nadler et al. |
| 6,866,668 B2 | 3/2005 | Giannetti et al. |
| 6,911,212 B2 | 6/2005 | Gertzman et al. |
| 6,932,977 B2 | 8/2005 | Heidaran et al. |
| 6,933,326 B1 | 8/2005 | Griffey et al. |
| 6,949,252 B2 | 9/2005 | Mizuno et al. |
| 7,033,587 B2 | 4/2006 | Halvorsen et al. |
| 7,041,641 B2 | 5/2006 | Rueger et al. |
| 7,045,141 B2 | 5/2006 | Merboth et al. |
| 7,067,123 B2 | 6/2006 | Gomes et al. |
| 7,070,942 B2 | 7/2006 | Heidaran et al. |
| 7,078,232 B2 | 7/2006 | Konkle et al. |
| RE39,321 E | 10/2006 | MacPhee et al. |
| 7,115,146 B2 | 10/2006 | Boyer, II et al. |
| 7,137,989 B2 | 11/2006 | Asculai et al. |
| 7,163,563 B2 | 1/2007 | Schwartz et al. |
| 7,179,299 B2 | 2/2007 | Edwards et al. |
| 7,201,917 B2 | 4/2007 | Malaviya et al. |
| 7,217,294 B2 | 5/2007 | Kusanagi et al. |
| 7,323,445 B2 | 1/2008 | Zhang et al. |
| 7,358,284 B2 | 4/2008 | Griffey et al. |
| 7,361,195 B2 | 4/2008 | Schwartz et al. |
| 2001/0005592 A1 | 6/2001 | Bhatnagar et al. |
| 2001/0006634 A1 | 7/2001 | Zaleske et al. |
| 2001/0010023 A1 | 7/2001 | Schwartz et al. |
| 2001/0016646 A1 | 8/2001 | Rueger et al. |
| 2001/0020188 A1 | 9/2001 | Sander |
| 2001/0031254 A1 | 10/2001 | Bianchi et al. |
| 2001/0039457 A1 | 11/2001 | Boyer et al. |
| 2001/0039458 A1 | 11/2001 | Boyer, II et al. |
| 2001/0051834 A1 | 12/2001 | Frondoza et al. |
| 2002/0009805 A1 | 1/2002 | Nevo et al. |
| 2002/0045940 A1 | 4/2002 | Giannetti et al. |

| | | | |
|---|---|---|---|
| 2002/0106393 A1 | 8/2002 | Bianchi et al. | |
| 2002/0111695 A1 | 8/2002 | Kandel | |
| 2002/0177224 A1 | 11/2002 | Madry et al. | |
| 2002/0192263 A1 | 12/2002 | Merboth et al. | |
| 2003/0021827 A1 | 1/2003 | Malaviya et al. | |
| 2003/0023316 A1 | 1/2003 | Brown et al. | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0040113 A1 | 2/2003 | Mizuno et al. | |
| 2003/0044444 A1 | 3/2003 | Malaviya et al. | |
| 2003/0049299 A1 | 3/2003 | Malaviya et al. | |
| 2003/0050709 A1 | 3/2003 | Noth et al. | |
| 2003/0078617 A1 | 4/2003 | Schwartz et al. | |
| 2003/0099620 A1 | 5/2003 | Zaleske et al. | |
| 2003/0144743 A1 | 7/2003 | Edwards et al. | |
| 2003/0229400 A1 | 12/2003 | Masuda et al. | |
| 2003/0236573 A1 | 12/2003 | Evans et al. | |
| 2004/0028717 A1 | 2/2004 | Sittinger et al. | |
| 2004/0033212 A1 | 2/2004 | Thomson et al. | |
| 2004/0044408 A1 | 3/2004 | Hungerford et al. | |
| 2004/0062753 A1 | 4/2004 | Rezania et al. | |
| 2004/0134502 A1 | 7/2004 | Mizuno et al. | |
| 2004/0138748 A1 | 7/2004 | Boyer, II et al. | |
| 2004/0143344 A1 | 7/2004 | Malaviya et al. | |
| 2004/0151705 A1 | 8/2004 | Mizuno et al. | |
| 2004/0166169 A1 | 8/2004 | Malaviya et al. | |
| 2004/0170610 A1 | 9/2004 | Slavin et al. | |
| 2004/0175826 A1 | 9/2004 | Maor | |
| 2004/0192605 A1 | 9/2004 | Zhang et al. | |
| 2004/0197311 A1 | 10/2004 | Brekke et al. | |
| 2004/0197373 A1 | 10/2004 | Gertzman et al. | |
| 2004/0219182 A1 | 11/2004 | Gomes et al. | |
| 2004/0220574 A1 | 11/2004 | Pelo et al. | |
| 2004/0230303 A1 | 11/2004 | Gomes et al. | |
| 2005/0004672 A1 | 1/2005 | Pafford et al. | |
| 2005/0027307 A1 | 2/2005 | Schwartz et al. | |
| 2005/0043814 A1 | 2/2005 | Kusanagi et al. | |
| 2005/0064042 A1 | 3/2005 | Vunjak-Novakovia et al. | |
| 2005/0074476 A1 | 4/2005 | Gendler et al. | |
| 2005/0074481 A1 | 4/2005 | Brekke et al. | |
| 2005/0089544 A1 | 4/2005 | Khouri et al. | |
| 2005/0112761 A1 | 5/2005 | Halvorsen et al. | |
| 2005/0129668 A1 | 6/2005 | Giannetti et al. | |
| 2005/0159820 A1 | 7/2005 | Yoshikawa et al. | |
| 2005/0159822 A1 | 7/2005 | Griffey et al. | |
| 2005/0196460 A1 | 9/2005 | Malinin | |
| 2005/0209705 A1 | 9/2005 | Niederauer et al. | |
| 2005/0222687 A1 | 10/2005 | Vunjak-Novakovia et al. | |
| 2005/0260612 A1 | 11/2005 | Padmini et al. | |
| 2006/0099234 A1 | 5/2006 | Winkler | |
| 2006/0111778 A1 | 5/2006 | Michalow | |
| 2006/0167483 A1 | 7/2006 | Asculai et al. | |
| 2006/0210643 A1 | 9/2006 | Truncale et al. | |
| 2006/0216822 A1 | 9/2006 | Mizuno et al. | |
| 2006/0247790 A1 | 11/2006 | McKay | |
| 2006/0276907 A1 | 12/2006 | Boyer, II et al. | |
| 2007/0009610 A1 | 1/2007 | Syring | |
| 2007/0014867 A1 | 1/2007 | Kusanagi et al. | |
| 2007/0065943 A1 | 3/2007 | Smith et al. | |
| 2007/0098759 A1 | 5/2007 | Malinin | |
| 2007/0148242 A1 | 6/2007 | Vilei et al. | |

FOREIGN PATENT DOCUMENTS

| | | | |
|---|---|---|---|
| EP | 0762903 B1 | 6/1995 | |
| EP | 0762903 A1 | 12/1995 | |
| EP | 0784985 A1 | 7/1997 | |
| EP | 0968012 A1 | 9/1998 | |
| EP | 1719531 A2 | 5/2001 | |
| EP | 1237511 A1 | 6/2001 | |
| EP | 1237511 B1 | 6/2001 | |
| EP | 1127585 A1 | 8/2001 | |
| EP | 1181908 A1 | 2/2002 | |
| EP | 1234552 A1 | 8/2002 | |
| EP | 1234555 A2 | 8/2002 | |
| EP | 1384452 A1 | 1/2004 | |
| EP | 1234555 A3 | 6/2004 | |
| EP | 1618178 A1 | 11/2004 | |
| EP | 1127581 B1 | 6/2005 | |
| EP | 1234552 B1 | 8/2006 | |
| EP | 0968012 B1 | 9/2006 | |
| EP | 1719463 A1 | 11/2006 | |
| EP | 1719532 A2 | 11/2006 | |
| EP | 1234555 B1 | 2/2007 | |
| EP | 0762903 B2 | 8/2007 | |
| WO | WO 84/04880 A1 | 12/1984 | |
| WO | WO 94/03584 A1 | 2/1994 | |
| WO | WO 95/33502 A1 | 12/1995 | |
| WO | WO 98/14222 A1 | 4/1998 | |
| WO | WO 98/41246 A2 | 9/1998 | |
| WO | WO 99/11298 A2 | 3/1999 | |
| WO | WO 99/21497 A1 | 5/1999 | |
| WO | WO 99/22747 A1 | 5/1999 | |
| WO | WO 99/48541 A1 | 9/1999 | |
| WO | WO 99/52572 A1 | 10/1999 | |
| WO | WO 01/43667 A1 | 6/2001 | |
| WO | WO 02/058484 A2 | 8/2002 | |
| WO | WO 03/007805 A2 | 1/2003 | |
| WO | WO 03/007805 A3 | 1/2003 | |
| WO | WO 03/007879 A2 | 1/2003 | |
| WO | WO 2004/075940 A1 | 9/2004 | |
| WO | WO 2004/096983 A2 | 11/2004 | |
| WO | WO 2004/096983 A3 | 11/2004 | |
| WO | WO 2004/103224 A1 | 12/2004 | |
| WO | WO 2005/110278 A2 | 11/2005 | |
| WO | WO 2005/110278 A3 | 11/2005 | |
| WO | WO 2006/042311 A2 | 4/2006 | |
| WO | WO 2006/042311 A3 | 4/2006 | |
| WO | WO 2007/024238 A1 | 3/2007 | |

OTHER PUBLICATIONS

Hunziker "Articular Cartilage Repair: Basic Science and Clinical Progress. A Review of the Current Status and Prospects", Osteoarthritis and Cartilage 2001, vol. 10, No. 6, pp. 432-463.

Chen et al., "Repair of Articular Cartilage Defects: Part I. Basic Science of Cartilage Healing", The American Journal of Orthopedics, Jan. 1999, pp. 31-33.

Chen et al., "Repair of Articular Cartilage Defects: Part II. Treatment Options", The American Journal of Orthopedics, Feb. 1999, pp. 88-96.

Buckwalter, "Articular Cartilage Injuries", Clinical Orthopedics and Related Research, 2002, No. 402, pp. 21-37.

Nixon et al., "New Horizons in Articular Cartilage Repair", Proceedings of the Annual Convention of the AAEP, 2001, vol. 47, pp. 217-226.

Tsumaki et al. "Role of CDMP-1 in Skeletal Morphogenesis: Promotion of Mesenchymal Cell Recruitment and Chondrocyte Differentiation", J. Cell Biol., Jan. 1999, vol. 144, No. 1, 161-173.

Feczko et al., "Experimental Results of Donor Site Filling for Autologous Osteochondral Mosaicplasty", Arthroscopy: The Journal of Arthroscopic and Related Surgery, vol. 19, No. 7 (Sep. 2003), pp. 755-761.

Peretti et al., "Cell-Based Bonding of Articular Cartilage: An Extended Study", Journal of Biomedical Materials Research, 64A, 2003, pp. 517-524.

Peretti et al., "Cell-based Tissue-Engineered Allogeneic Implant for Cartilage Repair" Tissue Engineering, 2000, vol. 6, No. 5, pp. 567-576.

Bugbee, "Fresh Osteochondral Allografting", Operative Techniques in Sports Medicine, Apr. 2000, vol. 8, No. 2, pp. 158-162.

Jackson et al., "Cartilage Substitutes: Overview of Basic Science & Treatment Options", Journal of American Academy of Orthopaedic Surgeons, vol. 9, Jan./Feb. 2001, pp. 37-52.

Verbruggen et al., "Repair Function in Organ Cultured Human Cartilage. Replacement of Enzymatically Removed Proteoglycans During Longterm Organ Culture", The Journal of Rheumatology, 12:4, 1985, pp. 665-674.

Glowacki, "Engineered Cartilage, Bone, Joints and Menisci—Potential for Temporomandicular Joint Reconstruction", Cells Tissues Organs, vol. 169, Issue 3, 2001, pp. 302-308.

Peretti et al., "A Biomechanical Analysis of an Engineered Cell-Scaffold Implant for Cartilage Repair", Annals of Plastic Surgery, 2001, vol. 46, No. 5, pp. 533-537.

Peretti et al., "Biomechanical Analysis of a Chondrocyte-Based Repair Model of Articular Cartilage", Tissue Engineering, Aug. 1, 1999, vol. 5, No. 4, pp. 317-326.

Peretti et al., "In Vitro Bonding of Pre-seeded Chondrocytes", Sport Sciences for Health, May 1, 2007, vol. 2, No. 1, pp. 29-33.

Peretti et al., "Bonding of Cartilage Matrices with Cultured Chondrocytes: An Experimental Model", Journal of Orthopaedic Research, Jan. 1998, vol. 16, No. 1, pp. 89-95.

USPTO Communication mailed Oct. 9, 2007 in connection with U.S. Appl. No. 10/438,883.

Non-final Office Action mailed on Nov. 5, 2004 2007 in connection with U.S. Appl. No. 10/438,883.

Non-final Office Action mailed on May 3, 2005 in connection with U.S. Appl. No. 10/438,883.

Final Office Action mailed on Oct. 18, 2005 in connection with U.S. Appl. No. 10/438,883.

Non-final Office Action mailed on Feb. 6, 2007 in connection with U.S. Appl. No. 10/438,883.

Office Action mailed Feb. 7, 2008 in connection with U.S. Appl. No. 10/815,778.

Non-final Office Action mailed on Feb. 20, 2007 in connection with U.S. Appl. No. 10/960,960.

Final Office Action mailed on Sep. 28, 2007 in connection with U.S. Appl. No. 10/960,960.

U.S. Appl. No. 12/010,984, filed Jan. 31, 2008.

U.S. Appl. No. 11/657,042, filed Jan. 24, 2007.

U.S. Appl. No. 12/043,001, filed Mar. 5, 2008.

International Search Report issued in connection with International Patent Application No. PCT/US2004/010957 Application on Nov. 1, 2004.

International Patent Application No. PCT/US2008/051796 filed Jan. 23, 2008.

Written Opinion issued on Nov. 1, 2004 in connection with International Patent Application No. PCT/US2004/010957.

International Preliminary Report on Patentability issued on Nov. 18, 2005 in connection with International Patent Application No. PCT/US2004/010957.

International Search Report issued in connection with International Patent Application No. PCT/US2005/030610 on Apr. 7, 2006.

Written Opinion issued on Apr. 7, 2006 in connection with International Patent Application No. PCT/US2005/030610.

International Preliminary Report on Patentability issued on Feb. 26, 2008 in connection with International Patent Application No. PCT/US2005/030610.

International Search Report issued in connection with International Patent Application No. PCT/US2005/036878 on Sep. 21, 2006.

Written Opinion issued on Sep. 21, 2006 in connection with International Patent Application No. PCT/US2005/036878.

International Preliminary Report on Patentability issued on Apr. 17, 2007 in connection with International Patent Application No. PCT/US2005/036878.

International Search Report issued in connection with International Patent Application No. PCT/US2005/008798 on Jun. 19, 2006.

International Search Report issued in connection with International Patent Application No. PCT/US2004/010956 on Oct. 28, 2005.

Written Opinion issued on Oct. 28, 2005 in connection with International Patent Application No. PCT/US2004/010956 on Oct. 28, 2005.

International Preliminary Report on Patentability issued on Nov. 18, 2005 in connection with International Patent Application No. PCT/US2004/010956.

Trzeciak et al., "Evaluation of Cartilage Reconstruction by Means of Autologous Chondrocyte Versus Periosteal Graft Transplantation: An Animal Study", Transplantation Proceedings, vol. 38 (2006), pp. 305-311.

Brighton et al., "Articular Cartilage Preservation and Storage—I. Application of Tissue Culture Techniques to the Storage of Viable Articular Cartilage", Arthritis and Rheumatism, vol. 22, No. 10 (Oct. 1979) pp. 1093-1101.

Mahadev et al., "Autogenous Osteochondral Morselised Grafts for Full Thickness Osteochondral Defects in the Knee Joint of Pigs", Singapore Medical Journal, 2001, vol. 42(9), pp. 410-416.

Hunziker, "Articular Cartilage Structure in Humans and Experimental Animals", *Articular Cartilage and Osteoarthritis*, Raven Press, ed., 1992, pp. 183-199.

Girotto et al., "Tissue-specific gene expression in chondrocytes grown on three-dimensional hyaluronic acid scaffolds", Biomaterials, vol. 24 (2003), pp. 3265-3275.

Gertzman et al., "A pilot study evaluating sodium hyaluronate as a carrier for freeze-dried demineralized bone powder", Cell and Tissue Banking, vol. 2, 2001, pp. 87-94.

Diduch et al., "Joint Repair: Treatment Options for Articular Cartilage Injury", Orthopedic Technology Review (2002) 4:24-27.

Stone et al., "One-Step American Technique of Articular Cartilage Paste Grafting to Traumatic and Arthritic Defects in the Knee Joint (2-7 Years Follow Up)", downloaded from http://www.stoneclinic.com/onestep.htm, publication date unknown.

U.S. Appl. No. 12/079,629, filed Mar. 26, 2008 titled Cartilage Implant Plug With Fibrin Glue and Method for Implantation.

Nettles et al., "In Situ Crosslinkable Hyaluronan For Articular Cartilage Repair", 50th Annual Meeting of the Orthopaedic Research Society, Paper No. 2020.

Nettles et al., "Photocrosslinkable Hyaluronan As a Scaffold for Articular Cartilage Repair", Annals of Biomedical Engineering, vol. 32, No. 3, Mar. 2004, pp. 391-397.

* cited by examiner

CARTILAGE ALLOGRAFT PLUG

RELATED APPLICATIONS

This is a continuation-in-part application of U.S. patent application Ser. No. 10/438,883 filed May 16, 2003.

FIELD OF INVENTION

The present invention is generally directed toward an implant and is more specifically directed toward an allograft implant having a cartilage face and bone body which has been treated to remove cellular debris and proteoglycans and is shaped so that the bone portion of the implant has an interference fit implantation in the existing bone while the cartilage face of the implant is spaced a distance ranging from 10 microns to 1000 microns away from the surrounding existing cartilage surface.

BACKGROUND OF THE INVENTION

Articular cartilage injury and degeneration present medical problems to the general population which are constantly addressed by orthopedic surgeons. Every year in the United States, over 500,000 arthroplastic or joint repair procedures are performed These include approximately 125,000 total hip and 150,000 total knee arthroplastics and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril meshwork, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint If the lining becomes worn or damaged resulting in lesions, joint movement may be painful or severely restricted. Whereas damaged bone typically can regenerate successfully, hyaline cartilage regeneration is quite limited.

Articular cartilage lesions generally do not heal, or heal only partially under certain biological conditions due to the lack of nerves, blood vessels and a lymphatic system. The limited reparative capabilities of hyaline cartilage usually result in the generation of repair tissue that lacks the structure and biomechanical properties of normal cartilage. Generally, the healing of the defect results in a fibrocartilaginous repair tissue that lacks the structure and biomechanical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage and are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of durable hyaline-like tissue that withstands normal joint loading and activity over prolonged periods. Currently, the techniques most widely utilized clinically for cartilage defects and degeneration are not articular cartilage substitution procedures, but rat lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone opens access of the host's marrow derived stem cells and induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age obtained good clinical results, which most likely reflects the decreasing population of osteochondral progenitor cells with increasing age. There have also been problems with fixation and stability of the grafts, which result in their displacement or loss from the repair site.

Transplantation of cells grown in culture provides another method of introducing a new cell population into chondral and osteochondral defects. Carticel® is a commercial process to culture the patient's own cartilage cells for use in the repair of cartilage defects in the knee joint marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks to achieve a 10 fold increase in cell mass. Once cultivated, the autologous cells are injected during an open and extensive knee procedure into areas of defective cartilage where it is hoped that they will facilitate the repair of damaged tissue. An autologous periosteal flap with cambium layer facing down is used to seal the transplanted cells in place and act as a mechanical barrier. Fibrin glue is used to seal the edges of the flap. This technique preserves the subchondral bone plate. Proponents of this procedure report that it produces satisfactory results, including the ability to return to demanding physical activities, in more than 80% of patients and that biopsy specimens of the tissue in the graft sites show hyaline-like cartilage repair. However, long term studies of this procedure in rabbits and dogs showed limited success and showed degradation at the implant site. The original study report has been criticized for not being a prospective controlled randomized study and for lack of quantitative or mechanical data. Of interest, a 14 year follow-up of a similar patient group that underwent diagnostic arthroscopy in combination with one of several treatments (removal of bone bodies, shaving, Pride drilling) had good to excellent knee function in 78% of the patients. Thus, further studies are needed to assess the function and durability of the new tissue to determine whether it improves joint function and delays or prevents joint degeneration.

As with the perichondrial graft, patient/donor age may compromise the success of this procedure as the chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint This technique, shown in Prior Art FIG. 2, can be performed as arthroscopic or open procedures. Reports of results of osteochondral plug autografts in a small numbers of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of 50% for 35 days at 4° C.

A number of United States Patents have been specifically directed towards bone plugs which are implanted into a bone defect Examples of such bone plugs are U.S. Pat. No. 4,950, 296 issued Aug. 21, 1990 which discloses a bone graft device comprising a cortical shell having a selected outer shape and a cavity formed therein for receiving a cancellous plug, and a cancellous plug fitted into the cavity in a manner to expose at least one surface; U.S. Pat. No. 6,039,762 issued Mar. 21, 2000 having a cylindrical shell with an interior body of deactivated bone material and U.S. Pat. No. 6,398,811 issued Jun. 4, 2002 directed toward a bone spacer which has a cylindrical cortical bone plug with an internal throughgoing bore designed to hold a reinforcing member. U.S. Pat. No. 6,383, 211 issued May 7, 2002 discloses an invertebral implant having a substantially cylindrical body with a throughgoing bore dimensioned to receive bone growth materials.

U.S. Pat. No. 6,379,385 issued Apr. 30, 2002 discloses an implant base body of spongious bone material into which a load carrying support element is embedded. The support element can take the shape of a diagonal cross or a plurality of cylindrical pins. See also, U.S. Pat. No. 6,294,187 issued Sep. 25, 2001 which is directed to a load bearing osteoimplant made of compressed bone particles in the form of a cylinder. The cylinder is provided with a plurality of throughgoing bores to promote blood flow through the osteoimplant or to hold a demineralized bone and glycerol paste mixture. U.S. Pat. No. 6,096,081 issued Aug. 1, 2000 shows a bone dowel with a cortical end cap or caps at both ends, a brittle cancerous body and a throughgoing bore.

A number of patents in the prior art show the use of bone putty, pastes or gels to fill bone defects. U.S. Pat. No. 5,290, 558 issued Mar. 1, 1994 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

A bone gel is disclosed in the U.S. Pat. No. 5,073,373 issued Dec. 17, 1991. Bone lamellae in the shape of threads or filaments retaining low molecular weight glycerol carrier are disclosed in U.S. Pat. Nos. 5,314,476 issued May 24, 1994 and 5,507,813 issued Apr. 16, 1996 and the tissue forms described in these patents are known commercially as the GRAFTON® Putty and Flex, respectively.

U.S. Pat. No. 5,356,629 issued Oct. 18, 1994 discloses making a rigid gel in the nature of a bone cement to fill defects in bone by mixing biocompatible particles, preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used.

U.S. Pat. No. 4,172,128 issued Oct. 23,1979 discloses a demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the patent notes that mucopolysaccharides produce pronounced ionotropic effects and that hyaluronic acid is particularly responsible for spatial cross-linking U.S. Pat. No. 6,030,635 issued Feb. 29, 2000 and U.S. Pat. No. 6,437,018 issued Aug. 20, 2002 are directed toward a malleable bone putty and a flowable gel composition for application to a bone defect site to promote new bone growth at the site which utilize a new bone growth inducing compound of demineralized lyophilized allograft bone powder. The bone powder has a particle size ranging from about 100 to about 850 microns and is mixed in a high molecular weight hydrogel carrier which contains a sodium phosphate saline buffer.

The use of implants for cartilage defects is much more limited than that for bone defects. Aside from the fresh allograft implants and autologous implants, U.S. Pat. No. 6,110,209 issued Nov. 5, 1998 shows the use of an autologous articular cartilage cancerous bone paste to fill arthritic defects. The surgical technique is arthroscopic and includes debriding (shaving away loose or fragmented articular cartilage), followed by morselizing the base of the arthritic defect with an awl until bleeding occurs. An osteochondral graft is then harvested from the inner rim of the intercondylar notch using a trephine. The graft is then morselized in a bone graft crusher, mixing the articular cartilage with the cancellous bone. The paste is then pushed into the defect and secured by the adhesive properties of the bleeding bone. The paste can also be mixed with a cartilage stimulating factor, a plurality of cells, or a biological glue. All patients are kept non-weight bearing for four weeks and used a continuous passive motion machine for six hours each night. Histologic appearance of the biopsies have mainly shown a mixture of fibrocartilage with hyaline cartilage. Concerns associated with this method are harvest site morbidity and availability, similar to the mosaicplasty method.

U.S. Pat. No. 6,379,367 issued Apr. 30, 2002 discloses a plug with a base membrane, a control plug, and a top membrane which overlies the surface of the cartilage covering the defective area of the joint.

U.S. Pat. No. 6,488,033 issued Dec. 3, 2002 discloses an allograft plug with a cartilage cap which is surface contour matched to the surface of a condyle defect area which is to be replaced. The allograft plug is transplanted in an interference fit within the cavity site which remains after a condylar defect is removed from a patients condyle.

SUMMARY OF THE INVENTION

A cartilage allograft construct assembly comprising a plug with a subchondral bone base and a smaller cross sectional cartilage cap for repairing articular cartilage defects is used together with a milled cartilage in a biocompatible carrier forming a paste or gel which is added to the plug or placed in a channel formed between the cartilage cap and a wall of a bore which has been cut into the patient to remove the lesion defect area. Additives may be applied to the cartilage mixture in order to increase chondrocyte migration and proliferation. Each allograft construct can support the addition of a variety of chondrogenic stimulating factors including, but not limited to growth factors (FGF-2, FGF-5, FGF-7, FGF-9, IGF-1, TGF-$\beta$, BMP-2, BMP-7, PDGF, PRP, VEGF), recombinant and native growth factors, human allogenic or autologous chondrocytes, human allogenic or autologous bone marrow cells, stem cells, demineralized bone matrix, insulin, insulin-like growth factor-1, transforming growth factor-B, interleukin-1 receptor antagonist, hepatocyte growth factor, platelet-derived growth factor, Indian hedgehog, parathyroid hormone-related peptide, bioactive glue and viral vectors or particles from adeno-associated virus for carrying genes from growth factor, DNA, marked DNA, RNAi, biological and other types of nanoparticles that can code for DNA or cytokines.

It is an object of the invention to provide an allograft implant for joints which provides pain relief, restores normal function and will postpone or alleviate the need for prosthetic replacement.

It is also an object of the invention to provide a cartilage repair implant which is easily placed in a defect area by the surgeon using an arthroscopic, minimally invasive technique.

It is still another object of the invention to provide an allograft implant which has load bearing capabilities.

It is further an object of the invention to provide an allograft implant procedure which is applicable for both partial and full thickness lesions.

It is yet another object of the invention to provide an allograft implant which facilitates growth of hyaline cartilage.

It is an additional object of the invention to provide implant plugs together with paste and gel formulations that satisfy surgical requirements and are made from available allograft tissue, some of which would otherwise be considered waste and thrown away.

These and other objects, advantages, and novel features of the present invention will become apparent when considered with the teachings contained in the detailed disclosure along with the accompanying drawings.

DESCRIPTION OF TH INVENTION

The term "tissue" is used in the general sense herein to mean any transplantable or implantable tissue, the survivability of which is improved by the methods described herein upon implantation. In particular, the overall durability and longevity of the implant are improved, and host-immune system mediated responses, are substantially eliminated.

The terms "transplant" and "implant" are used interchangably to refer to tissue, material or cells (xenogeneic or allogeneic) which may be introduced into the body of a patient to replace or supplement the structure or function of the endogenous tissue.

Figure 1:
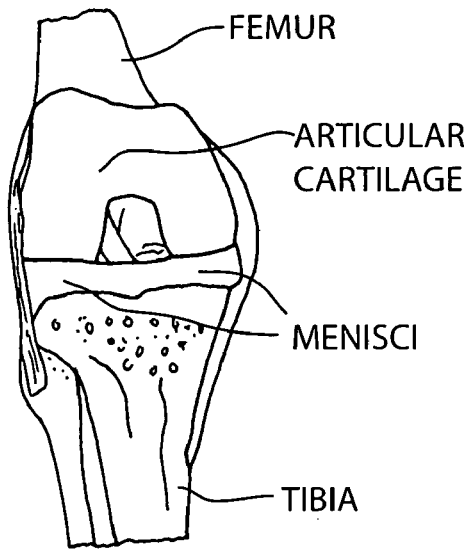
FIG. 1 shows the anatomy of a knee joint.
Figure 2:
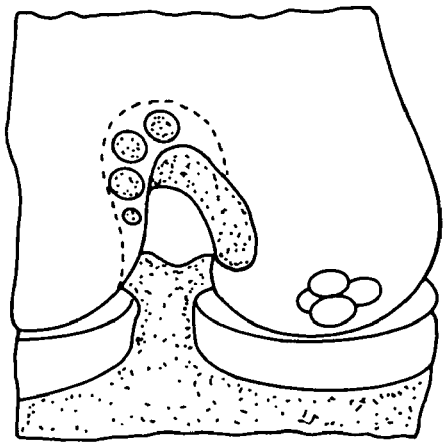
FIG. 2 shows a schematic mosaicplasty as known in the prior art.
Figure 3:
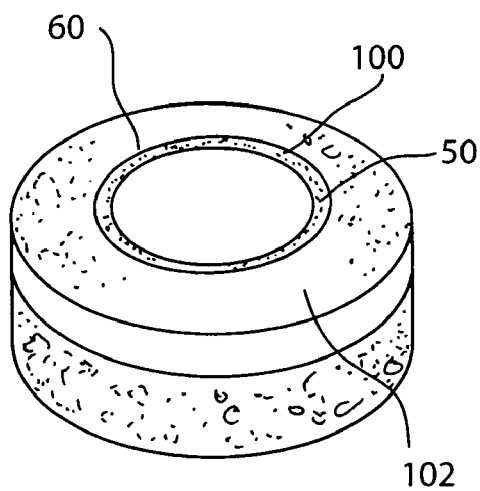
FIG. 3 shows a schematic perspective view of an interference fit cylindrical allograft osteochondral plug assembly shown in FIG. 4 in a schematic defect site.
Figure 4:
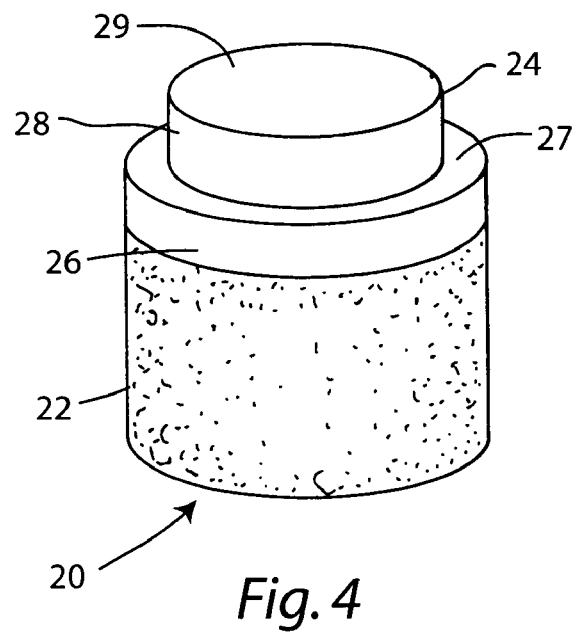
FIG. 4 shows an enlarged perspective view of a cylindrical subchondral bone interference fit allograft osteochondral plug having a stepped cartilage cap.

The terms "autologous" and "autograft" refer to tissue or cells which originate with or are derived from the recipient, whereas the terms "allogeneic" and "allograft" refer to cells and tissue which originate with or are derived from a donor of the same species as the recipient. The terms "xenogeneic" and "xenograft" refer to cells or tissue which originates with or are derived from a species other than that of the recipient The present invention is directed towards a cartilage repair assembly and method of treatment The preferred embodiment and best mode of the invention is shown in FIGS. 3 and 4. In the production of the invention, an allograft implant plug having a subchondral bone body portion 22 and an overlying cap 24 of hyaline cartilage is treated to remove cellular material, chondrocytes and pluripotent mesenchymal cells and proteoglycans. The plug is then frozen within a range of −20° C. to −100° C., preferably −70° C. and lyophilized reducing its water content.

In the treatment for cell, chondrocyte and proteoglycan extraction the allograft cartilage and plugs which were previously harvested from a donor were soaked in hyaluronidase (type IV-s, 3 mg/mL), trypsin (0.25% in monodibasic buffer 3 ml) and the samples were placed in a test tube for 18 hours at 37° C. with sonication. It was found that sonication is not a necessary requirement and the times of soaking vary with concentration of hyaluronidase and trypsin and can be as little as 2 hours. The plug samples were decalcified, washed w/DI water and placed in a 50%/50% chloroform/methanol solution for 72 hours to remove cellular debris, proteoglycans and sterilize. The above method has been previously used on human tissue and is set forth in the Journal of Rheumatology, 12:4, 1985 by Gust Verbruggen et al titled Repair Function in Organ Cultured Human Cartilage Replacement of Enzymatically Removed Proteoglycans During Longterm Organ Culture. After repeated washes with sterile DI water, the hydrated plug samples and cartilage were frozen at −70° C. and lyophilized to reduce the water content within the range of about 0.1% to about 8.0%. In an alternative usage, the plug samples and cartilage were frozen after processing.

The osteochondral plug 20 which has been treated as noted above has a subchondral bone portion 22 and an overlying integral cartilage cap 24 and is placed in a blind bore or core 60 as shown in FIG. 3 which has been cut in the lesion area of the bone 100 of a patient with the upper portion of the cartilage cap 24 being cut away to form a stepped configuration with the bottom step 26 having a plannar upper surface 27 and a diameter the same as the cylindrical subchondral bone portion 22. The cylindrical top step portion 28 has a diameter smaller than that of step 26 with a flat or slightly rounded upper surface 29 corresponding to the configuration of the surface of the original cartilage 102 remaining at the lesion area being treated. The length of the osteochondral plug 20 can be the same as the depth of the bore 60 or less than the depth of the bore 60. If the plug 20 is the same length, the base of the plug implant is supported and the upper surface of the articular cartilage cap is level with the articular cartilage 102. If the plug is of a lesser length, the base of the plug implant is not supported but support is provided by the wall of the bore 60 or respective cut out area as the bone portion of the plug is interference fit within the bore or cut out area with the cap being surface aligned with the articular cartilage surface 102. With such load bearing support the graft surface is not damaged by weight or bearing loads which can cause micromotion interfering with the graft interface producing fibrous tissue interfaces and subchondral cysts.

Figure 6:
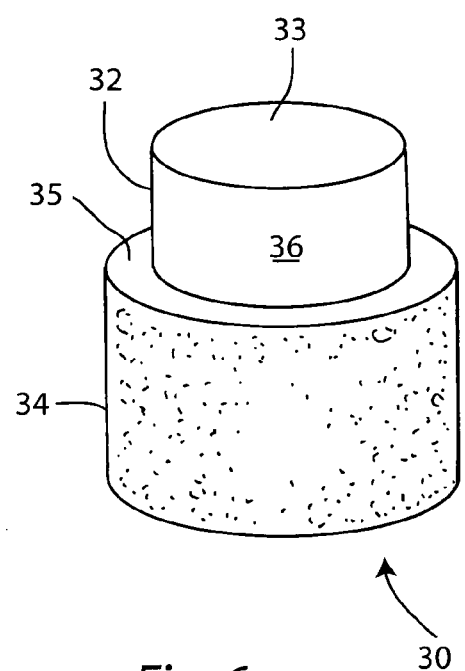
FIG. 6 shows an enlarged perspective view of an allograft osteochondral plug with a cylindrical cartilage cap having a stepped configuration and an interference fit subchondral bone portion of the plug.

The bone portion 22 thus has an interference fit within bore 60 adjacent the subchondral bone layer of the bore and the cartilage cap 24 is spaced away from the cartilage layer of bore 60 forming a ring shaped gap or channel 50 having a width ranging between 10 microns and 1000 microns and more preferably between 100 microns and 500 microns and a depth which may differ as shown by the configurations shown in FIGS. 4 and 6. If desired, the step may be cut down adjacent to the top of the bone while leaving a thin layer of cartilage 35 as is shown in FIG. 6. This provides an osteochondral plug 30 having an articular cartilage cylindrical shaped cap 32 with a top surface 33 substantially aligned to the surface of the original cartilage 102. Since the cap 32 has a smaller diameter than that of the integral cylindrical bone portion 34, the cap cylinder outer surface 36 forms with the bore 60 sidewall, a ring shaped channel 50 into which a milled cartilage mixture and other additives can be placed. This channel has the same width as previously noted.

Figure 5:
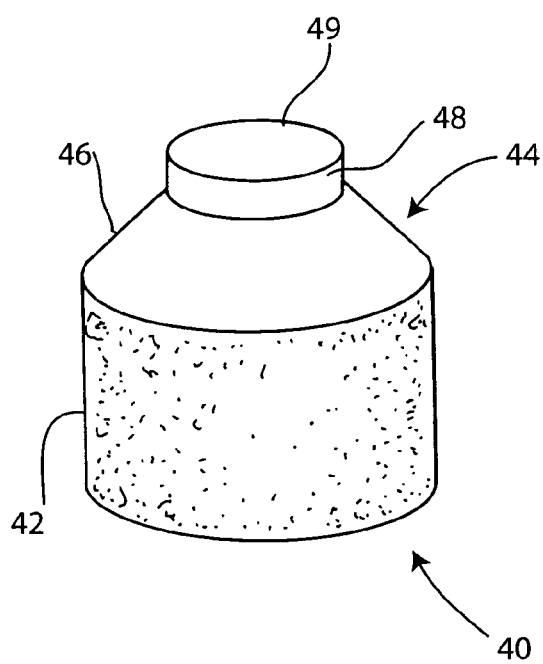
FIG. 5 shows an enlarged perspective view of a cylindrical subchondral bone interference fit osteochondral plug having a tapered cartilage cap with a cylindrical end portion.

Another variant of the above is the implant plug 40 shown in FIG. 5. Implant plug 40 has a cylindrical subchondral bone portion 42 and an overlying smaller diameter cartilage cap 44. The cap 44 has tapered conical sidewalls forming a frustum conical section 46 and a smaller diameter cylindrical top cap section 48 having a top surface 49. Thus, a ring shaped channel 50 with an inclined bottom surface defined by tapered surface 46 is formed when the plug 40 is inserted in the bore 60 to receive the milled or minced allograft cartilage biological carrier mixture and additives. This channel has the same range of widths as previously noted.

In operation the lesion or defect is removed by cutting a cylindrical bore 60 removing a lesion in the implant area 100 and filling the channel 50 and optionally a portion of the bore 60 or cut away area with a desired amount of a milled allograft cartilage mixture and a biological carrier such as sodium hyaluronate, hyaluronic acid and its derivatives, gelatin, collagen, chitosan, alginate, buffered PBS, Dextran, or polymers. One or more additives namely chondrogenic stimulating factors including, but not limited to growth factors (FGF-2, FGF-5, FGF-7, FGF-9, IGF-1, TGF-β, BMP-2, BMP-7, PDGF, VEGF), recombinant as well as native growth factors, human allogenic or autologous chondrocytes, human allogenic cells, human allogenic or autologous bone marrow cells, human allogenic or autologous stem cells, demineralized bone matrix, insulin, insulin-like growth factor-1, interleukin-1 receptor antagonist, hepatocyte growth factor, platelet-derived growth factor, Indian hedgehog, parathyroid hormone-related peptide, viral vectors or particles from adeno-associated virus used to carry genes from growth factor, DNA delivery, naked DNA, RNAi, biological and other types of nanoparticles that can code for DNA or cytokines can be added to the allograft cartilage mixture. The mixture will have the consistency of a paste or gel.

If desired demineralized or partially demineralized bone powder having a size range from 200 to 850 microns with a weight ranging from 1% to 35% of the cartilage mixture can be added to the milled cartilage glue mixture 30. Either autologous or allogeneic cells can be deposited into the defect area but preferably allogeneic cells such as chondrocytes are added in a range of 10 million to 500 million cells per cc of mixture, with a preferable range of 10 million to 100 million and a more preferably range of 20 to 40 million cells or the cell solution may be deposited directly onto the defect area prior to insertion of the plug and in the channel between the plug and the bore wall after the plug has been deposited.

Suitable organic glue material can optionally be used to keep the implant fixed in place in the implant area Suitable organic glue material can be found commercially, such as for example; TISSEEL® or TISSUCOL.® (fibrin based adhesive; Immuno AG, Austria), Adhesive Protein (Sigma Chemical, USA), Dow Corning Medical Adhesive B (Dow Corning, USA), fibrinogen thrombin, elastin, collagen, casein, albumin, keratin and the like.

EXAMPLE 1

A non-viable or decellularized osteochondral plug consisting of a subchondral cylindrical bone base and overlying smaller diameter cylindrical cartilage cap cut from the original plug block was treated with a solution or variety of solutions such as hyaluronidase (type IV-5), trypsin and a chloroform/methanol to remove the cellular debris as well as the proteoglycans as noted in the treatment described above. It is believed that this removal provides signaling to stimulate the surrounding chondrocytes to proliferate and form new proteoglycans and other factors producing new matrix. The plug is then subjected to an antibiotic soak as shown and milled to a configuration shown in the drawing to have an interference fit for the bore size cut in the patient. The diameter of the cylindrical subchondral bone portion of the plug ranges from 1 mm to 30 mm but is preferably 3 mm to 10 mm which is small enough to fit through the endoscopic cannula, but large enough to minimize the number of plugs needed to fill large defects. This size provides good results at the recipient site and provides a more confluent hyaline surface. The thickness of subchondral bone can be modified to match the anatomy of the patient so that the surface cartilage of the plug will be even with and follow the surface contour of the surface cartilage of the host tissue. The treated plug also creates a more porous matrix, which allows more cells to enter. The plug and minced hyaline cartilage can be stored frozen or freeze dried and support any of the mentioned chondrogenic stimulating factors. The plug can be inserted arthroscopically similar to the mosaicplasty procedure or through an open incision. The plug and cartilage material can be made in various dimensions depending on the size of the defect being treated.

This plug uses the allograft cartilage putty or gel as noted below in a prepackaged amount to fill channel 50 and provide cartilage cell growth for the osteochondral plug from the outer diameter of the cartilage cap to the inner wall of the bore hole in the surrounding cartilage material. The putty or gel enhances the tissue integration between the plug and host tissue.

The base of the bore or cut away area and the gap or space formed by the exterior of the cartilage cap and bore wall forming channel 50 is provided with a matrix of minced cartilage putty consisting of minced or milled allograft cartilage which has been lyophilized so that its water content ranges from 0.1% to 8.0% ranging from 25% to 50% by weight, mixed with a carrier of sodium hyaluronate solution (HA) (molecular weight ranging from $7.0 \times 10^5$ to $1.2 \times 10^6$) or any other bioabsorbable carrier such as hyaluronic acid and its derivatives, gelatin, collagen, chitosan, alginate, buffered PBS, Dextran, polymers, and synthetic and peptide based hydrogels, the carrier ranging from ranging from 75% to 50% by weight. The cartilage is milled to a size ranging up to 1 mm.

In gel form, the minced cartilage has been lyophilized so that its water content ranges from 0.1% to 8.0%, ranging from 15% to 30% by weight and the carrier ranges from 85% to 70% by weight. The particle size of the cartilage when milled is less than or equal to 1 mm dry. The cartilage pieces can be processed to varying particle sizes and the HA or other carrier can have different viscosities depending on the desired consistency of the putty or gel. This cartilage matrix can be deposited into the cartilage defect arthroscopically and fit into the defect where it is held in place by the implant which is placed over it as a cap.

Alternatively, cells which have been grown outside the patient are inserted by syringe into the implant site prior to, during or after deposit of the cartilage matrix into the defect area Such cells include allogenic or autologous bone marrow cells, stem cells and chondrocytes. The cellular density of the cells preferably ranges from $1.0 \times 10^8$ to $5.0 \times 10^8$ or from about 100 million to about 500 million cells per cc of putty or gel mixture. This composite material can be injected into the cartilage defect arthroscopically as previously noted. This matrix can support the previously mentioned chondrogenic stimulating factors.

It is also envisioned that the minced cartilage pieces and/or the osteochondral plug implant can be coated with a solution containing adeno-associated virus vectors (AAV) or recombinant adeno-associated virus (rAAV) containing a growth gene. An AAV contains only two genes, a rep gene which codes for proteins involved in DNA replication and the other is a cap gene which by differential splicing codes for the three proteins that make up the protein coat of the virus.

The operation of placing the cartilage defect assembly in a cartilage defect, comprises (a) drilling a cylindrical hole in a patient at a site of a cartilage defect to remove the diseased area of cartilage; (b) placing the pretreated implant bore in interference with the wall of the bore; and (c) placing a mixture of milled allograft cartilage in a bioabsorbable carrier in a channel formed between the cut allograft cartilage cap and the cartilage layer of the drilled cylindrical hole.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. In combination, minced cartilage putty comprising milled cartilage pieces mixed in a biocompatible carrier and a sterile, cylindrically-shaped allograft bone plug, said plug including a subchondral bone portion, which has a diameter selected to form an interference fit against a subchondral bone layer exposed as a result of a bore formed in a defect area in articular cartilage of a host, and an integral overlying cartilage cap which has been treated to remove cellular debris, chondrocytes and proteoglycans, said cap having a first cap portion, which is located proximal to said subchondral bone portion of said plug, said first cap portion having a diameter the same as that of said subchondral bone portion of said plug, and a second cap portion, which is located remote from said subchondral bone portion of said plug and which has a diameter less than that of said subchondral bone portion of said plug, said first and second cap portions being separated by an annular step which forms a ring-shaped gap positionable alongside a cartilage layer exposed as a result of a bore formed in a defect area in articular cartilage of a host, said gap being sized and shaped so as to receive said minced cartilage putty for promoting cartilage cell growth in said gap and for enhancing tissue integration between said plug and host tissue, when said plug is inserted into a bore formed in a defect area in articular cartilage of a host.

2. The combination as claimed in claim 1, wherein said first cap portion has a cylindrical shape, and said second can portion has a cylindrical shape.

3. The combination as claimed in claim 1, wherein said first cap portion has a frustum conical shape and said second cap portion has a cylindrical shape.

4. The combination as claimed in claim 3, wherein said first cap portion includes a small diameter end positioned adjacent said second cap portion, and a large diameter end positioned adjacent said subchondral bone potion.

5. The combination as claimed in claim 1, wherein said milled cartilage pieces are individually sized pieces having a size less than 1 mm.

6. The combination as claimed in claim 5, wherein said milled cartilage pieces are derived from hyaline cartilage.

7. The combination as claimed in claim 1, further comprising a chondrogenic stimulating factor mixed with said milled cartilage pieces and said biocompatible carrier.

8. The combination as claimed in claim 7, wherein said chondrogenic stimulating factor is one or more of a group consisting of growth factors (FGF-2, FGF-5, FGF-7, FGF-9, IGF-1, TGF-β, BMP-2, BMP-7, PDGF, PRP, VEGF), recombinant, native growth factors, human allogenic or autologous chondrocytes, human allogenic or autologous bane marrow cells, stem cells, demineralized bone matrix, insulin, insulin-like growth factor-1, transforming growth factor-B, interleukin-1 receptor antagonist, hepatocyte growth factor, platelet-derived growth factor, Indian hedgehog and parathyroid hormone-related peptide or bioactive glue.

9. The combination as claimed in claim 1, wherein said biocompatible carrier comprises one or more of a group consisting of sodium hyaluronate, hyaluronic acid and its derivatives, gelatin, collagen, chitosan, alginate, buffered PBS, Dextran, polymers, and synthetic and peptide based hydrogels.

10. The combination as claimed in claim 1, wherein said allograft bone plug has been lyophilized so that its water content ranges from about 0.1% to about 8.0%.

11. The combination as claimed in claim 1, wherein said allograft bone plug is coated with a solution containing an adeno-associated virus segment carrying a cartilage growth gene.

12. The combination as claimed in claim 1, wherein said allograft bone plug is coated with a solution containing an adeno-associated virus segment carrying at least one gene from a group consisting of growth factor, DNA, naked DNA, RNAi, biological and other types of nanoparticles that can code for DNA or cytokines.

13. The combination as claimed in claim 1, wherein said allograft bone plug is coated with a solution containing a recombinant adeno-associated virus segment carrying a cartilage growth gene.

14. The combination as claimed in claim 1, wherein when said ring-shaped gap has a width in a range from 50 microns to 1000 microns.

15. The combination as claimed in claim 1, wherein when said ring-shaped gap has a width in a range from 100 microns to 500 microns.

16. The combination as claimed in claim 1, wherein said allograft bone plug has been sterilized in an antibiotic soak.

17. The combination as claimed in claim 1, wherein the diameter of said second cap portion is in a range from about 200 microns to about 1000 microns less than the diameter of said subchondral bone portion.

18. A method of repairing an articular cartilage defect of a patient, said method comprising the steps of:
(a) providing a sterile, cylindrically-shaped allograft bone plug, the plug including a subchondral bone portion and an integral overlying cartilage cap which has been treated to remove cellular debris, chondrocytes and proteoglycans, the cap having a first cap portion, which is located proximal to the subchondral bone portion of the plug, the first cap portion having a diameter the same as that of the subchondral bone portion of the plug, and a second cap portion, which is located remote from the subchondral bone portion of the plug, the second cap portion having a diameter less than that of the subchondral bone portion of the plug, the first end second cap portions being separated by an annular step formed in the cartilage cap;
(b) forming a bore in an articular cartilage defect area of the patient, the bore exposing a subchondral bone layer and a cartilage layer in the defect area;
(c) inserting the plug into the bore so that (i) the subchondral bone portion of the plug forms an interference fit against the exposed subchondral bone layer and (ii) the second cap portion of the plug is spaced from the exposed cartilage layer to thereby cooperate with the annular step in the formation of a ring-shaped gap positioned alongside the exposed cartilage layer; and
(d) providing the ring-shaped gap with minced cartilage putty to promote cartilage cell growth in the gap and to enhance tissue integration between the plug and the patient's tissue, the cartilage putty comprising milled cartilage pieces mixed in a biocompatible carrier.

19. The method as claimed in claim 18, wherein the milled cartilage pieces have a size less than 1 mm.

20. The method as claimed in claim 19, wherein the milled cartilage pieces are derived from hyaline cartilage.

21. The method as claimed in claim 19, wherein the minced cartilage putty includes a chondrogenic stimulating factor mixed with the milled cartilage pieces and the biocompatible carrier.

22. The method as claimed in claim 18, wherein the diameter of the second cap portion is in a range from about 200 microns to about 1000 microns less than the diameter of said subchondral bone portion.

23. The method as claimed in claim 18, wherein the biocompatible carrier comprises one or more of a group consisting of sodium hyaluronate, hyaluronic acid and its derivatives, gelatin, collagen, chitosan, alginate, buffered PBS, Dextran, polymers, and synthetic and peptide based hydrogels.

24. The method as claimed in claim 18, further comprising a step of lyophilizing the plug so that its water content is in a range from about 0.1% to about 8.0%. said lyophilizing step being performed before said bore-forming step (b).

25. The method as claimed in claim 18, wherein the ring-shaped gap has a width in a range from 50 microns to 1000 microns.

26. The method as claimed in claim 18, wherein the ring-shaped gap has a width in a range from 100 microns to 500 microns.

* * * * *